(12) United States Patent
Cho et al.

(10) Patent No.: US 10,258,311 B2
(45) Date of Patent: Apr. 16, 2019

(54) PROBE, ULTRASOUND IMAGING APPARATUS, AND CONTROL METHOD OF THE ULTRASOUND IMAGING APPARATUS

(71) Applicant: SAMSUNG ELECTRONICS CO., LTD., Suwon-si (KR)

(72) Inventors: Kyungil Cho, Seoul (KR); Minseog Choi, Seoul (KR); Youngil Kim, Suwon-si (KR); Jong Keun Song, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 629 days.

(21) Appl. No.: 14/823,108

(22) Filed: Aug. 11, 2015

(65) Prior Publication Data

US 2016/0157818 A1 Jun. 9, 2016

(30) Foreign Application Priority Data

Dec. 8, 2014 (KR) ........................ 10-2014-0175069

(51) Int. Cl.
*A61B 8/00* (2006.01)
*A61B 8/08* (2006.01)
*G01S 15/89* (2006.01)
*B06B 1/06* (2006.01)
*G01S 7/52* (2006.01)

(52) U.S. Cl.
CPC .......... *A61B 8/4444* (2013.01); *A61B 8/4488* (2013.01); *A61B 8/5207* (2013.01); *B06B 1/0622* (2013.01); *G01S 7/52079* (2013.01); *G01S 15/8925* (2013.01); *A61B 8/4405* (2013.01); *A61B 8/461* (2013.01); *A61B 8/54* (2013.01)

(58) Field of Classification Search
CPC ........ B06B 3/00; B06B 1/0618; H03H 9/175; A61B 8/4488; A61B 8/4444; G01S 7/52079; G01S 15/8925
USPC ......................................... 310/334, 335, 336
See application file for complete search history.

(56) References Cited

U.S. PATENT DOCUMENTS

| | | | | |
|---|---|---|---|---|
| 7,750,537 B2 * | 7/2010 | Hossack | ............... | B06B 1/0629 310/334 |
| 2005/0017599 A1 * | 1/2005 | Puskas | ..................... | B01J 19/10 310/317 |
| 2010/0141093 A1 * | 6/2010 | Fraser | ................... | B06B 1/0207 310/334 |
| 2011/0254405 A1 * | 10/2011 | Zaitsu | ................... | B06B 1/0292 310/300 |
| 2013/0223192 A1 * | 8/2013 | Nishiwaki | .............. | H04B 11/00 367/135 |
| 2015/0057540 A1 * | 2/2015 | Sameshima | ............... | B06B 1/06 600/437 |
| 2015/0374336 A1 * | 12/2015 | Lee | ...................... | A61B 8/4494 600/459 |

* cited by examiner

*Primary Examiner* — Bryan P Gordon
(74) *Attorney, Agent, or Firm* — Sughrue Mion, PLLC

(57) ABSTRACT

A probe includes a transducer array including a transducer element, the transducer element including cells connected in parallel to each other, and a current detector configured to apply a voltage to the cells of the transducer element, or to output an electrical signal based on currents output from the cells.

14 Claims, 11 Drawing Sheets

(a)

(b)

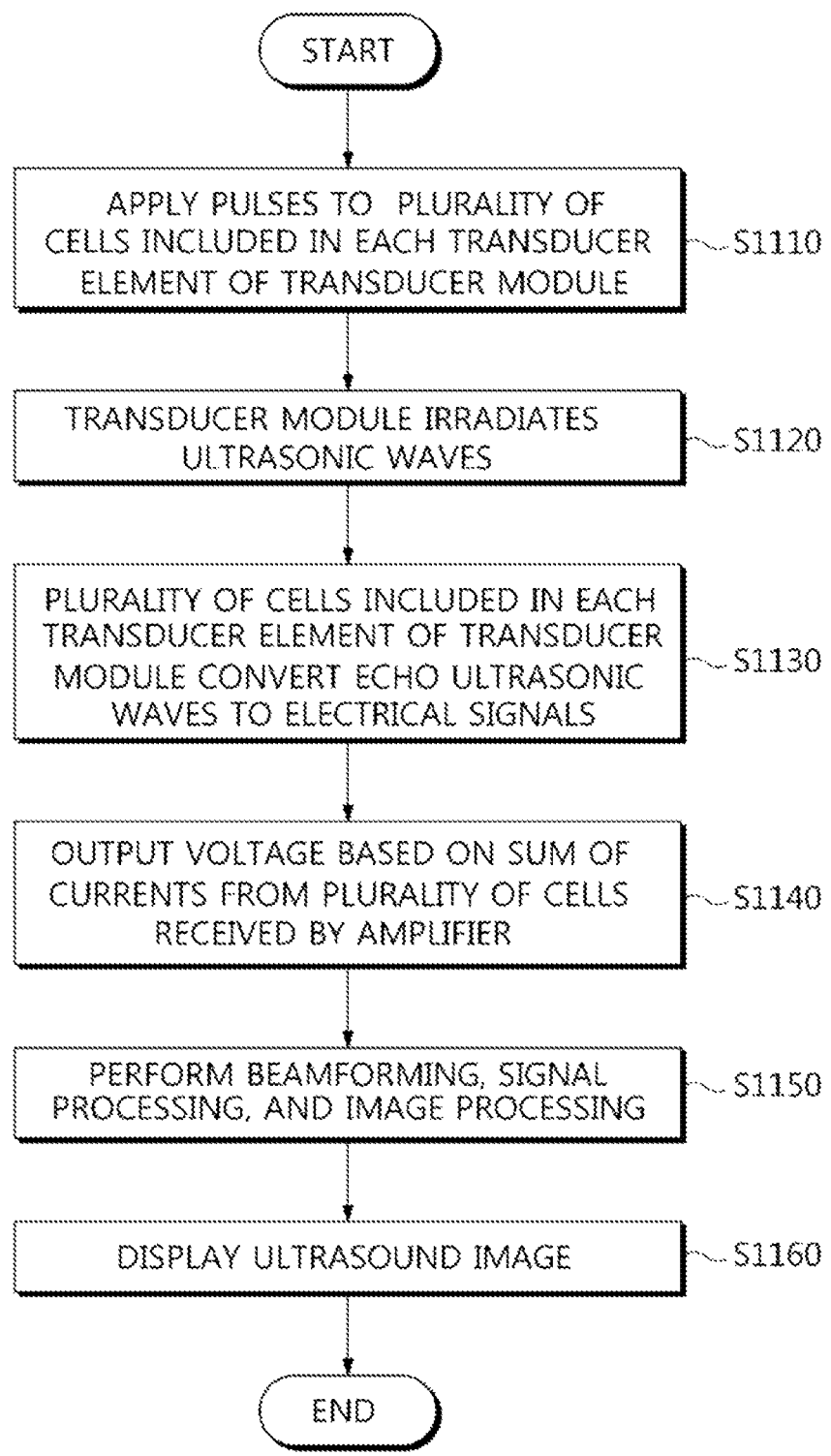

ized to PROBE, ULTRASOUND IMAGING
APPARATUS, AND CONTROL METHOD OF
THE ULTRASOUND IMAGING APPARATUS

CROSS-REFERENCE TO RELATED
APPLICATION

This application claims the benefit of Korean Patent Application No. 10-2014-0175069, filed on Dec. 8, 2014 in the Korean Intellectual Property Office, the disclosure of which is incorporated herein by reference in its entirety.

BACKGROUND

1. Field

Exemplary embodiments consistent with the present disclosure relate to a probe, an ultrasound imaging apparatus, and a control method of the ultrasound imaging apparatus.

2. Description of the Related Art

An ultrasound imaging apparatus irradiates ultrasonic signals to a target region inside an object from the surface of the object, and receives echo ultrasonic signals reflected from the target region so as to non-invasively acquire slice images about soft tissue of the object or images about blood vessels of the object based on the echo ultrasonic signals.

The ultrasound imaging apparatus has advantages that the ultrasound imaging apparatus is a compact, low-priced apparatus and can display images in real time, compared to other medical imaging apparatuses, such as an X-ray apparatus, a Computerized Tomography (CT) scanner, a Magnetic Resonance Image (MRI) apparatus, and the like. Due to these advantages, the ultrasonic diagnostic apparatus is widely used to diagnose the heart, abdomen, urinary organs, uterus, and other physical objects.

SUMMARY

Therefore, it is an aspect of the exemplary embodiments to provide a probe configured to generate an electrical signal based on currents output from a plurality of transducer elements, each transducer element configured with a plurality of cells to transmit or receive ultrasonic waves to or from an object, an ultrasound imaging apparatus, and a control method of the ultrasound imaging apparatus.

Additional aspects of the exemplary embodiments will be set forth in part in the description which follows and, in part, will be obvious from the description, or may be learned by practice of the disclosure.

In accordance with an aspect of an exemplary embodiment, a probe includes: a transducer array comprising a transducer element, the transducer element comprising cells connected in parallel to each other; and a current detector configured to apply a voltage to the cells of the transducer element, or to output an electrical signal based on currents output from the cells.

The transducer element may include a piezoelectric micromachined ultrasonic transducer (pMUT) element, and the transducer array may include a pMUT array.

One of the cells may be made of thin-film lead zirconate titanate (PZT) having a thickness of 2.5 μm or less.

One of the cells may include a upper electrode, a lower electrode, and a thin-film piezoelectric device interposed between the upper electrode and the lower electrode, the upper electrode of the cell may be connected in parallel to upper electrodes of cells included in another transducer element, and the lower electrode of the cell may be connected in parallel to lower electrodes of the other cells included in the transducer element.

The upper electrodes of the cells of the transducer element and the other transducer element may be configured to receive a ground voltage or a direct current voltage applied in common to the upper electrodes of the cells of the transducer element and the other transducer element.

The lower electrodes of the cells of the transducer element and the other transducer element may be connected to the current detector.

The current detector may be configured to detect a voltage difference between the upper electrode and the lower electrode of the cell.

The cell may further include a board member provided on a side of the lower electrode opposite a side at which the upper electrode is provided, the board member being configured to support the lower electrode.

The board member may include a fixing support part formed along edges of the board member, and a membrane part formed in a center of the board member, the board member including silicon (Si), and the thin-film piezoelectric device may expand or contract in a traverse direction according to a voltage applied to the lower electrode to vibrate the membrane part.

An area of the upper electrode may occupy 70% or less of an area of the membrane part.

The transducer element may include a via configured to connect the upper electrodes of the cells to each other or to connect the lower electrodes of the cells to each other.

The transducer element may include four cells or nine cells.

The current detector may include an amplifier configured to output a voltage that is proportional to a sum of the currents output from the cells.

The probe may further include an analog-to-digital converter configured to convert an electrical signal output from the current detector into a digital signal.

In accordance with another aspect of an exemplary embodiment, a method of controlling an ultrasound imaging apparatus includes: receiving, at a transducer element comprising cells connected in parallel to each other, echo ultrasonic waves reflected from an object; generating an electrical signal corresponding to the echo ultrasonic waves; receiving, at a current detector, the electrical signal; and outputting a voltage based on a current included in the electrical signal.

The transducer element may include a piezoelectric micromachined ultrasonic transducer (pMUT) element.

One of the cells may include an upper electrode, a lower electrode, and a thin-film piezoelectric device interposed between the upper electrode and the lower electrode, and the method further includes, before performing the generating of the electrical signal, applying a ground voltage or a direct current voltage to the upper electrode of the cell.

The outputting of the voltage may include outputting a voltage based on a sum of currents included in electrical signals received from the cells connected in parallel to each other.

The outputting of the voltage may include converting the voltage into a digital signal.

Before generating the electrical signal, the method may further include: applying pulses to the transducer elements; and at the transducer elements, generating ultrasonic waves.

In accordance with another aspect of an exemplary embodiment, an ultrasound imaging apparatus includes: a transducer array comprising cells connected in parallel to each other; an integrated circuit configured to apply a voltage to the cells, or to output an electrical signal based on currents output from the cells; a signal processor configured to generate ultrasound image data based on the electrical signal output from the integrated circuit; and an image processor configured to generate an ultrasound image based on the ultrasound image data.

One of the cells may include an upper electrode, a lower electrode, and a thin-film piezoelectric device interposed between the upper electrode and the lower electrode, the upper electrode of the cell may be connected in parallel to upper electrodes of cells comprised in another transducer element, and the lower electrode of the cell may be connected in parallel to lower electrodes of other cells in the transducer element.

The integrated circuit may include an inverting amplifier configured to output a voltage that is proportional to a sum of the currents output from the plurality of cells.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 11 is a flowchart illustrating a method of controlling an ultrasound imaging apparatus, according to an exemplary embodiment.

DETAILED DESCRIPTION

Figure 1:
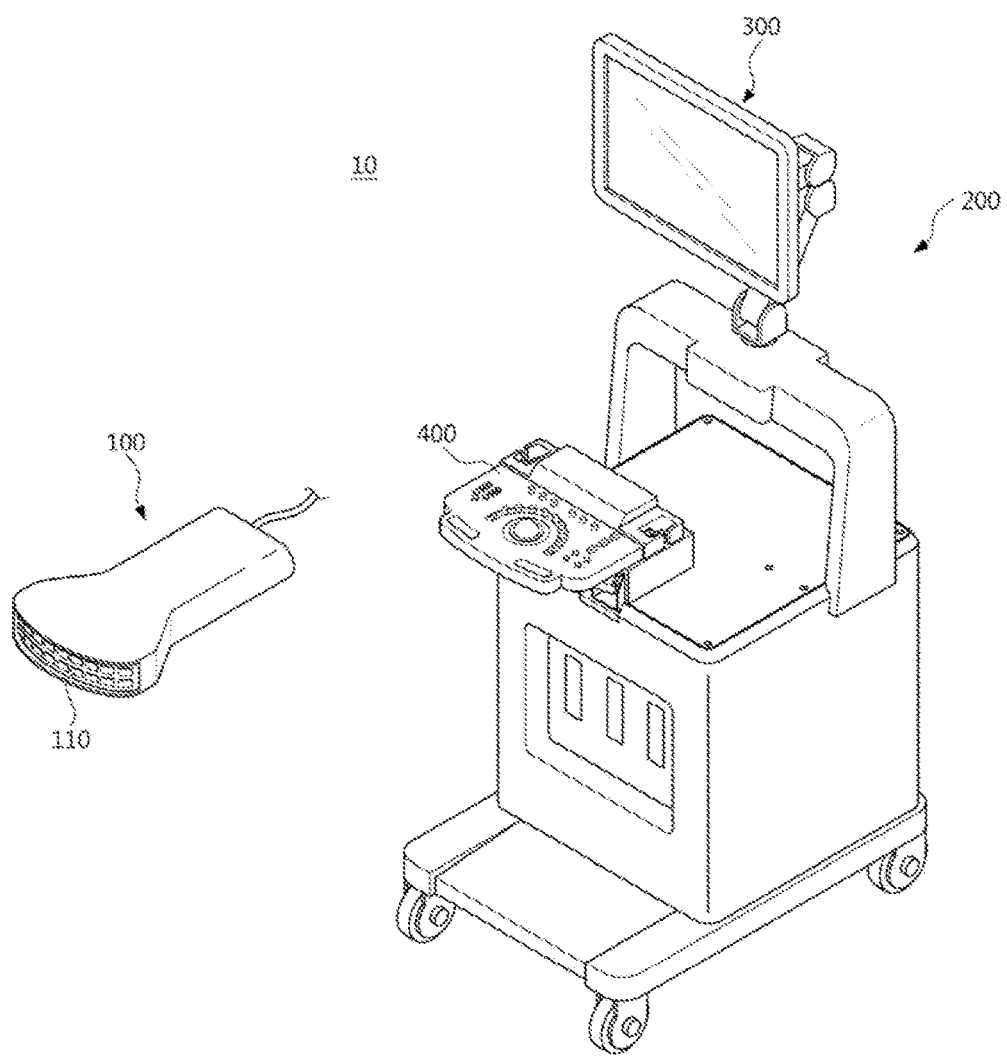
FIG. 1 is a perspective view of an ultrasound imaging apparatus according to an exemplary embodiment.

Purposes, specific advantages, and novel features of the exemplary embodiments will become apparent from the following detailed description and the accompanying drawings, which are associated with exemplary embodiments. In this specification, the same reference numerals are used throughout the different drawings to designate the same components. Further, when it is determined that the detailed description related to the exemplary embodiments may obscure the gist of the exemplary embodiments, the detailed description will be omitted. Also, it will be understood that, although the terms first, second, etc., may be used herein to describe various elements, these elements should not be limited by these terms. These terms are only used to distinguish one element from another.

Hereinafter, exemplary embodiments will be described in detail with reference to the appended drawings.

Figure 2:
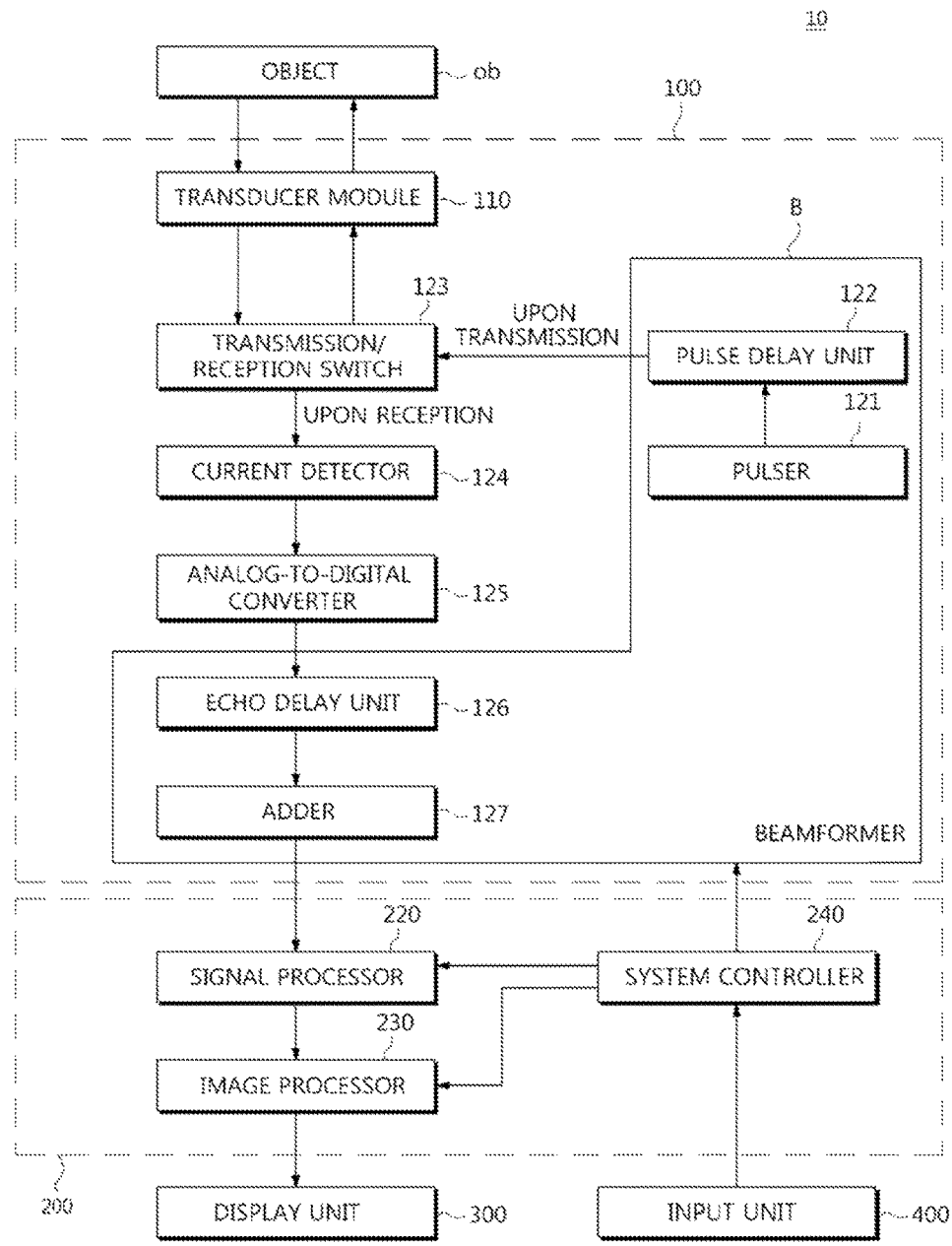
FIG. 2 is a control block diagram of an ultrasound imaging apparatus according to an exemplary embodiment.

FIG. 1 is a perspective view of an ultrasound imaging apparatus according to an exemplary embodiment, and FIG. 2 is a control block diagram of an ultrasound imaging apparatus according to an exemplary embodiment.

Referring to FIG. 1, an ultrasound imaging apparatus 10 may include a probe 100 configured to irradiate ultrasonic waves to an object ob, to receive echo ultrasonic waves reflected from the object ob, and to convert the echo ultrasonic waves into electrical signals (hereinafter, also referred to as ultrasound signals), and a main body 200 configured to create an ultrasound image based on the ultrasound signals. The main body 200 may be connected to the probe 100, and may be a workstation including a display unit 300 and an input unit 400.

Hereinafter, the configuration and operations of the ultrasound imaging apparatus 10 will be described with reference to FIG. 2.

The probe 100 includes a transducer module 110, a beamformer B, a transmission/reception switch 123, a current detector 124, and an analog-to-digital converter 125.

The transducer module 110 may generate ultrasonic waves according to pulses applied thereto, and irradiate the ultrasonic waves to the object ob. The ultrasonic waves irradiated to the object ob may be reflected from a target region inside the object ob. The transducer module 110 may receive echo ultrasonic waves reflected from the target region, and convert the received echo ultrasonic waves into electrical signals. A detailed configuration of the transducer module 110 will be described with reference to FIGS. 3 to 10, later.

The object may be a human's or animal's body part, or tissue in a body part, such as vessels, bonds, and muscles. However, the object is not limited to the above-mentioned body part or tissue, and may be anything whose inner structure can be imaged by the ultrasound imaging apparatus 10.

The beamformer B is used to apply appropriate delay times to ultrasonic waves to be irradiated or received echo ultrasonic waves, in order to focus ultrasonic waves generated by the transducer module 110 on a target region of the object ob at a desired time, or to compensate for the differences between times of arrival of echo ultrasonic waves reflected from the target region of the object ob at individual transducer elements 111b (see FIG. 4) included in the transducer module 110.

The beamformer B includes a pulser 121, a pulse delay unit 122 (e.g., pulse delayer), an echo delay unit 126 (e.g., echo delayer), and an adder 127.

The pulser 121 may generate an alternating current voltage (that is, pulses) for driving the transducer module 110 in order to irradiate ultrasonic waves.

There may be provided a plurality of pulsers 121 corresponding to the number of channels or the number of transducer elements 111b included in the transducer module 110.

Upon irradiation of ultrasonic waves, the transmission/reception switch 123 may operate in a transmission mode, and the pulser 121 may generate voltage pulses ranging from −80V to +80V or from 0V to 200V as transmission pulses, and transfer the transmission pulses to the individual transducer elements 111b configuring the transducer module 110.

The pulse delay unit 122 may apply delay times to the transmission pulses according to a focused point and a steering angle of the ultrasonic waves to form a transmission signal pattern.

Like the pulser 121, there may be provided a plurality of pulse delay units 122 corresponding to the number of channels or the number of the transducer elements 111b included in the transducer module 110.

The pulse delay unit 122 may apply appropriate delay times to the individual transducer elements 111b so that pulses generated by the individual pulsers 121 can arrive at a focused point. There may be a plurality of focused points forming a scan line. The voltage pulses delayed by the pulse delay unit 122 may be transferred as transmission pulses to the individual transducer elements 111b configuring the transducer module 110.

Upon reception of ultrasonic waves, the echo delay unit 126 may delay digital signals from the individual transducer elements 111b according to a focused point and a steering angle of the ultrasonic waves.

If the transmission/reception switch 123 operates in a reception mode after irradiation of ultrasonic waves is completed, and the transducer module 110 receives echo ultrasonic waves, the echo delay unit 126 may receive digital signals corresponding to the echo ultrasonic waves from the analog-to-digital converter 125, and delay the digital signals output from the individual transducer elements 111b included in the transducer module 110, based on the focused point and the steering angle of the ultrasonic waves with respect to the target region.

For example, the echo delay unit 126 may set a delay frequency, based on at least one of parameters indicating whether the transducer module 110 includes a 2-Dimensional (2D) transducer array, a focal depth, a steering angle, an aperture size, and the number of activated transducer elements 111b among the transducer elements 111b, and apply delay times to digital signals output from the individual transducer elements 111b included in the transducer module 110 according to the delay frequency.

The adder 127 may add the delayed digital signals, upon reception of ultrasonic waves.

More specifically, the adder 127 may add the digital signals output from the transducer elements 111b included in the transducer module 110, to which the delay times have been applied by the echo delay unit 126, and focus the result of the addition into a digital signal. The focused digital signal may be output from the probe 100 and transferred to a signal processor 220 of the main body 200. The signal processor 220 may perform signal processing on the focused digital signal, and transfer the signal-processed signal to an image processor 230. The image processor 230 may perform various image processing operations on the received signal to create an ultrasound image.

In the ultrasound imaging apparatus 10 shown in FIG. 2, the beamformer B is included in the probe 100 corresponding to a front-end. However, the beamformer B may be included in the main body 200 corresponding to a back-end. That is, the entire beamformer B or a part of components of the beamformer B may be included in any one of the front-end and the back-end.

The transmission/reception switch 123 may switch a mode to a transmission mode upon irradiation of ultrasonic waves, or to a reception mode upon reception of ultrasonic waves, according to a control signal received from a system controller 240 of the main body 200.

The current detector 124 may detect current output from the transducer module 110. The current detector 124 may be an amplifier to amplify a voltage according to current output from the transducer module 110.

The current detector 124 may further include a pre-amplifier (not shown) to amplify analog signals having small magnitudes. The pre-amplifier may be a Low Noise Amplifier (LNA).

Also, the current detector 124 may further include a Variable Gain Amplifier (VGA) (not shown) to control a gain value according to an input signal. The VGA may be Time Gain Compensation (TGC) to compensate for a gain according to a focused point or a distance to a focused point, although is not limited to being a TGC.

The analog-to-digital converter 125 may convert an analog voltage output from the current detector 124 into a digital signal.

In the exemplary embodiment of FIG. 2, the digital signal converted by the analog-to-digital converter 125 is input to the echo delay unit 126 of the beamformer B, however, an analog signal delayed by the echo delay unit 126 may be input to the analog-to-digital converter 126.

Also, in the exemplary embodiment of FIG. 2, the analog-to-digital converter 125 is included in the probe 100, however, the analog-to-digital converter 125 may be included in the main body 200. In this case, the analog-to-digital converter 125 may convert an analog signal focused by the adder 127 into a digital signal.

The main body 200 may accommodate components to control the probe 100 or to create an ultrasound image based on signals received from the probe 100. The main body 200 may be connected to the probe 100 through a cable.

Hereinafter, the signal processor 220, the image processor 230, and the system controller 240 included in the main body 200, the display unit 300, and the input unit 400 will be described.

The signal processor 220 may convert a focused digital signal received from the probe 100 into a format that is suitable for image processing. For example, the signal processor 220 may perform filtering for removing noise signals that are out of a predetermined frequency band.

The signal processor 220 may be a Digital Signal Processor (DSP). The signal processor 220 may perform envelop detection of detecting the magnitudes of echo ultrasonic waves based on the focused digital signal to thus generate ultrasound image data.

The image processor 230 may create an ultrasound image based on the ultrasound image data generated by the signal processor 220 so that a user, for example, a doctor or a patient, can visually examine the object ob, for example, the inside of a human body.

The image processor 230 may transfer the ultrasound image created based on the ultrasound image data to the display unit 300.

According to another exemplary embodiment, the image processor 230 may perform additional image processing on the ultrasound image. For example, the image processor 230 may further perform image post-processing of correcting or adjusting the contrast, brightness, or sharpness of the ultrasound image.

The image post-processing of the image processor 230 may be performed according to predetermined settings or according to a user's instruction or command received through the input unit 400.

The system controller 240 may control overall operations of the ultrasound imaging apparatus 10. For example, the system controller 240 may control operations of the signal processor 220, the image processor 230, the probe 100, and the display unit 300.

According to an exemplary embodiment, the system controller 240 may control operations of the ultrasound imaging apparatus 10 according to predetermined settings, or may generate a predetermined control command according to a user's instruction or command received through the input unit 400 to control operations of the ultrasound imaging apparatus 10.

The system controller 240 may include a processor, Read Only Memory (ROM) in which control programs for controlling the ultrasound imaging apparatus 10 are stored, and Random Access Memory (RAM) which stores signals or ultrasound image data received through the probe 200 or the input unit 400 or is used as a storage area for various tasks performed by the ultrasound imaging apparatus 10.

Also, the system controller 240 may be electrically connected to a graphic processing board on which a processor, RAM, or ROM is mounted.

The processor, the ROM, and the ROM may be connected to each other through internal buses.

Also, according to an exemplary embodiment, the term "system controller" may indicate a component including a processor, RAM, and ROM.

Also, according to an exemplary embodiment, the term "system controller" may indicate a component including a processor, RAM, ROM, and a processing board.

The display unit 300 may display an ultrasound image created by the image processor 230 so that a user can visually examine the inside structure or tissue of the object ob.

The input unit 400 may receive a predetermined instruction or command for controlling the ultrasound imaging apparatus 10 from a user. The input unit 400 may be a user interface, such as a keyboard, a mouse, a trackball, a touch screen, or a paddle.

Hereinafter, the configuration and operations of the transducer module 110 will be described in more detail with reference to FIGS. 3 and 4.

Figure 3:
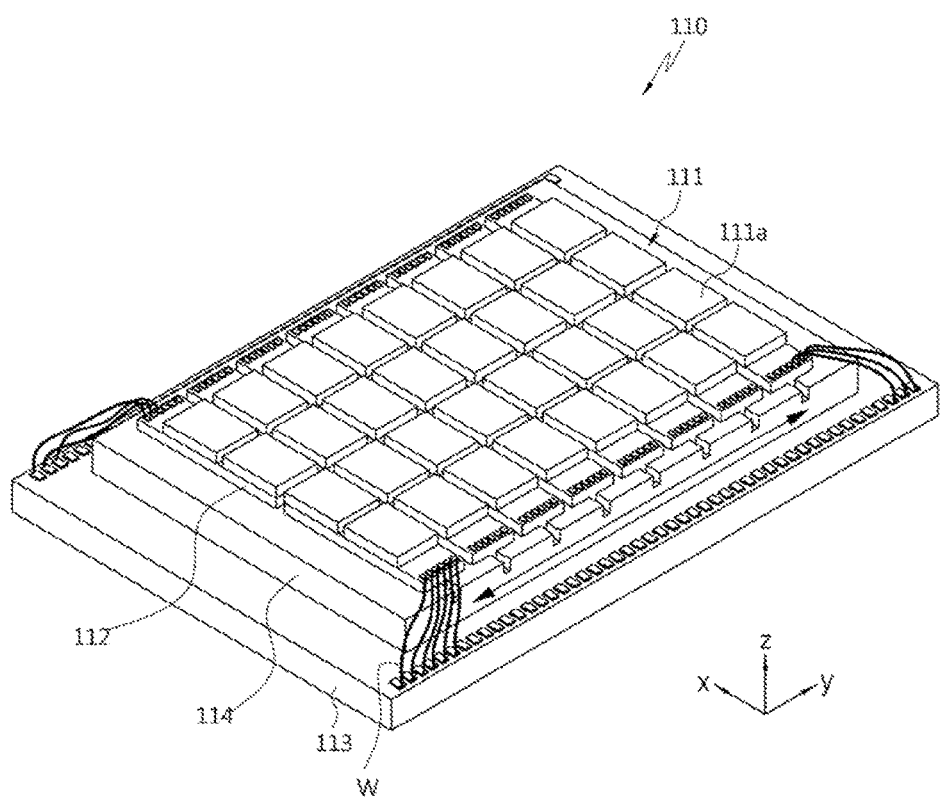
FIG. 3 is a perspective view showing an external appearance of a transducer module according to an exemplary embodiment.
Figure 4:
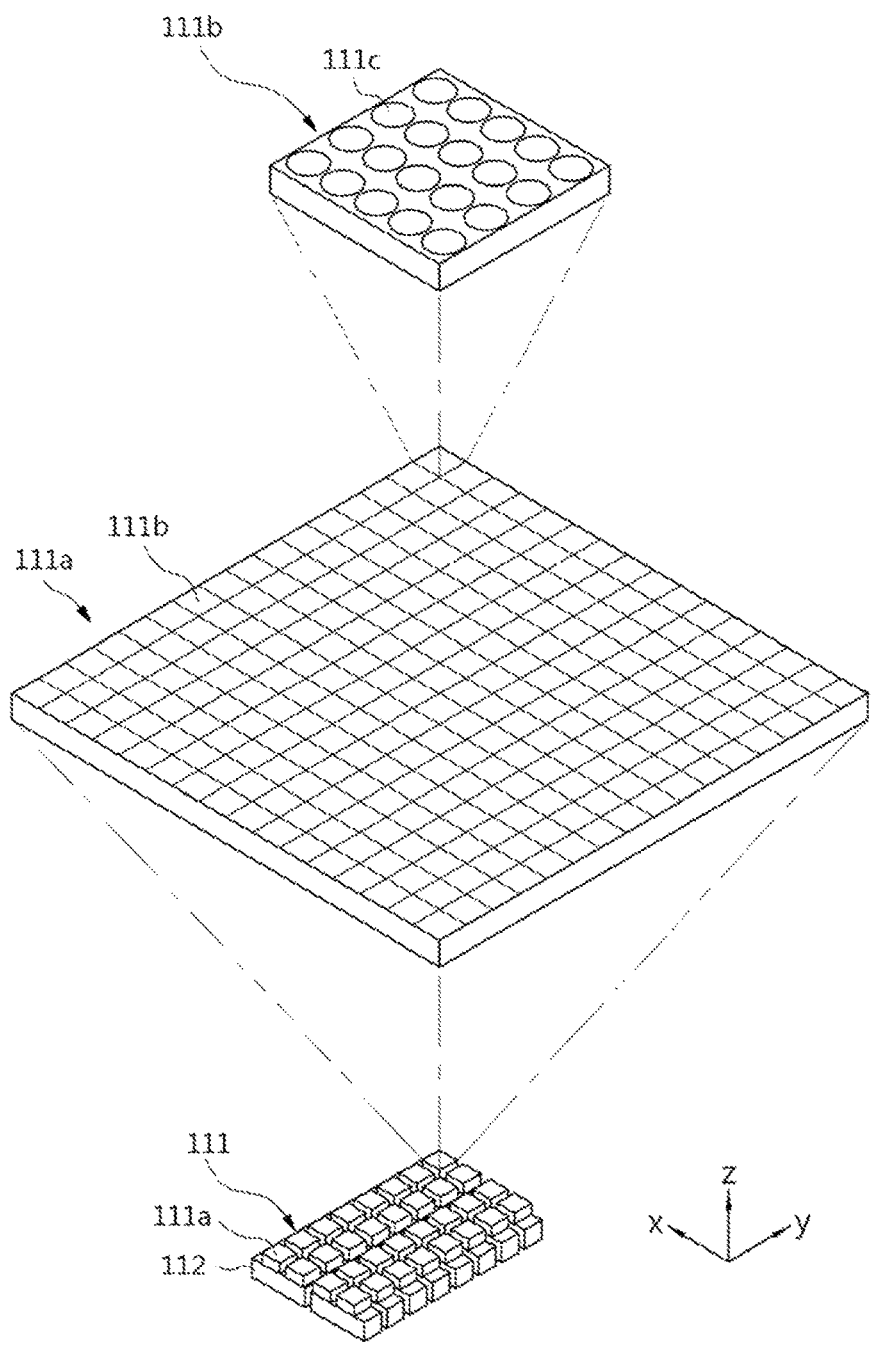
FIG. 4 is an enlarged view for describing a configuration of a transducer array of the transducer module shown in FIG. 3.

FIG. 3 is a perspective view showing an external appearance of the transducer module 110 according to an exemplary embodiment, and FIG. 4 is an enlarged view for describing a configuration of a transducer array included in the transducer module 110 of FIG. 3.

Referring to FIGS. 3 and 4, the transducer module 110 may include a transducer array 111, one or more integrated circuits 112, a control board 113, and a support member 114.

The transducer array 111 may be configured with a plurality of tiles 111a, and bonded on the integrated circuits 112. The transducer array 111 may be in the form of a 2D array.

The tiles 111a may be basic units configuring the transducer array 111. Each tile 111a may be configured with a plurality of transducer elements 111b arranged in the form of a 2D array.

Each transducer element 111b may include a plurality of cells 111c arranged in the form of a 2D array, wherein the cells 111c vibrate when electrical signals are applied thereto.

For example, the transducer array 111 may be a 2D array of a 4×8 size configured with 32 tiles 111a. Each tile 111a may be in the form of a 2D array of 16×16 size configured with 256 transducer elements 111b.

The transducer element 111b may be a magnetostrictive ultrasonic transducer using the magnetostrictive effect of a magnetic material widely used in a probe, a piezoelectric ultrasonic transducer or a piezoelectric micromachined ultrasonic transducer (pMUT) using the piezoelectric effect of a piezoelectric material, or a capacitive micromachined ultrasonic transducer (cMUT) that transmits and receives ultrasonic waves using vibration of several hundreds or thousands of micromachined thin films.

The configuration and operations of the transducer element 111b will be described in detail with reference to FIGS. 5 to 7, later.

The integrated circuit 112 may be implemented by integrating the beamformer B, the transmission/reception switch 123, the current detector 124, and the analog-to-digital converter 125 into Application Specific Integrated Circuits (ASIC). The integrated circuits 112 may be bonded with the transducer array 111 through flip-chip bonding.

The control board 113 may transmit control signals to the integrated circuits 112 according to a control signal from the system controller 240 of the main body 200, or receive electronic signals from the integrated circuits 112.

The control board 113 may be disposed below the integrated circuits 112 to be parallel to the integrated circuits 112 so that the control board 113 and the integrated circuits 112 form a laminated structure.

Also, the integrated circuits 112 may be connected to the control board 113 through wires W.

The control board 113 may generate a control signal, and may be implemented as a Printed Circuit Board (PCB) on which electronic devices for processing electrical signals are mounted.

The support member 114 may be in the form of a frame which is interposed between the integrated circuits 112 and the control board 113 and in which a plurality of grooves corresponding to the shapes of the tiles 111a of the transducer array 111 are formed to support the tiles 111a of the transducer array 111. As shown in FIG. 3, the support member 114 may include a plurality of grooves in which the integrated circuits 112 bonded with the tiles 111a configuring the transducer array 111 can be respectively provided.

Hereinafter, the configuration and operations of the transducer element 111b will be described in detail with reference to FIGS. 5 to 7. For convenience of description, the transducer element 111b is assumed to be pMUT, although it is understood that the transducer element 111b is not limited thereto.

Figure 5:
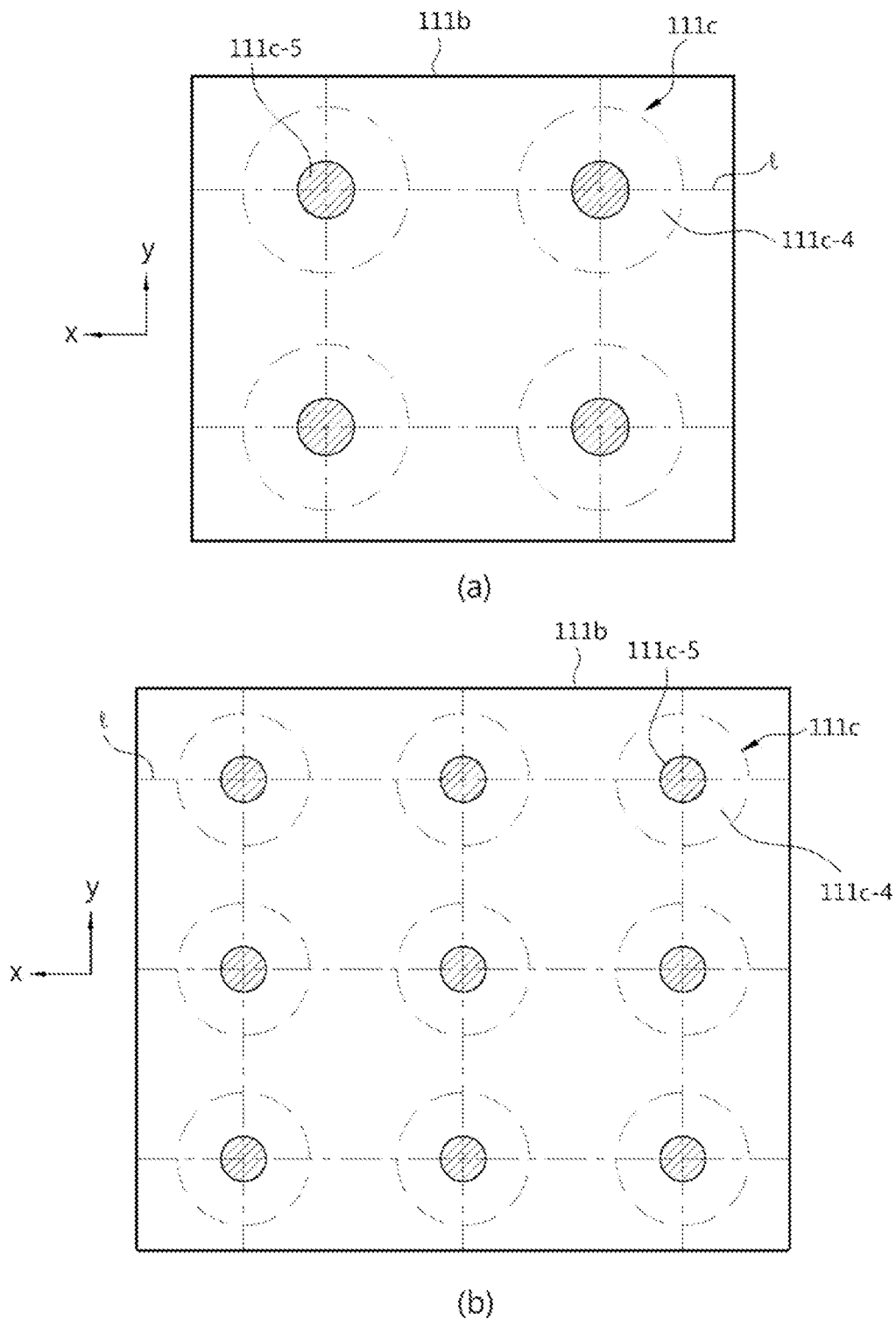
FIG. 5 is a front view of a transducer element seen in a z-axis direction based on the coordinate system of FIG. 4, according to an exemplary embodiment.
Figure 6:
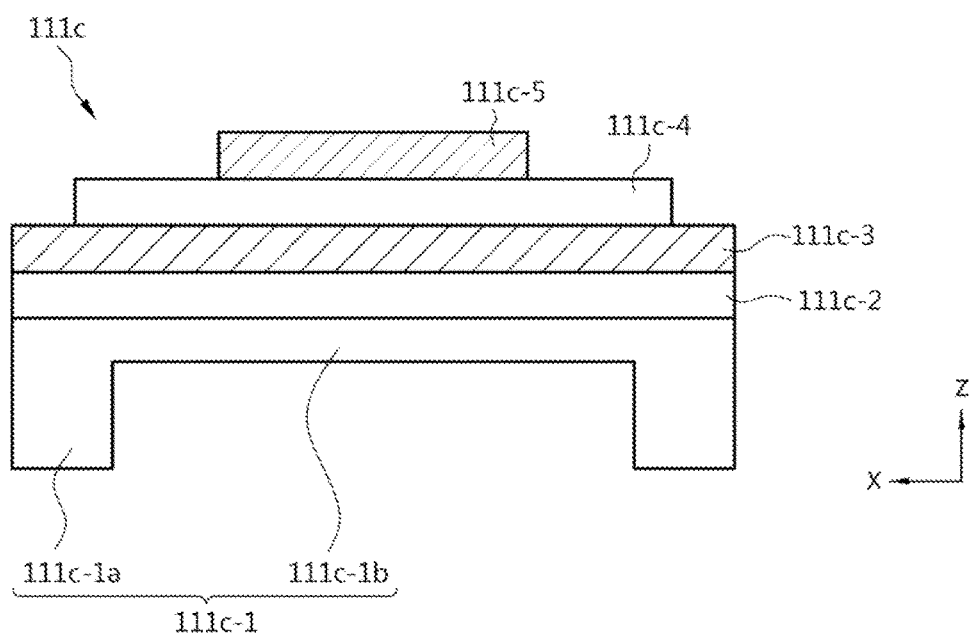
FIG. 6 is a cross-sectional view of a cell configuring a transducer element for describing a laminated structure of the cell.

FIG. 5 is a front view of the transducer element 111b seen in a z-axis direction based on the coordinate system of FIG. 4, according to an exemplary embodiment, and FIG. 6 is a cross-sectional view of a cell configuring the transducer element 111b for describing a laminated structure of the cell.

Referring to FIGS. 5 and 6, each transducer element 111b may be configured with a plurality of cells 111c.

The transducer element 111b may be configured with n×n (n is an integer) cells, such as four (2×2) cells (see (a) of FIG. 5) or nine (3×3) cells (see (b) of FIG. 5), although the number of cells is not limited thereto.

Each cell 111c may include a board member 111c-1, an insulating layer 111c-2, a lower electrode 111c-3, a piezoelectric device 111c-4, and an upper electrode 111c-5. The plurality of cells 111c configuring the transducer element 111b may be connected to each other through metal lines l, as shown in FIG. 5.

The board member 111c-1 may be disposed below the lower electrode 111c-3, and support the lower electrode 111c-3. The board member 111c-1 may include a fixing support part 111c-1a formed along the edges, and a membrane part 111c-1b formed in the center. The board member 111c-1 may be made of silicon (Si).

The fixing support part 111c-1a may support the corresponding cell 111c, and the membrane part 111c-1b may be implemented as a thin film that vibrates vertically by expansion or contraction in a traverse direction of the piezoelectric device 111c-4 to generate ultrasonic waves or to receive echo ultrasonic waves.

The insulating layer 111c-2 may be interposed between the lower electrode 111c-3 and the board member 111c-1. The insulating layer 111c-2 may be formed as a thin oxidized layer to insulate the lower electrode 111c-3 from the board member 111c-1. The insulating layer 111c-2 may be omitted as necessary.

The lower electrode 111c-3 may be positioned over the board member 111c-1, and receive or transmit electrical signals from or to the integrated circuit 112.

Due to the parallel connections between the cells 111c, pulses may be applied in common to the lower electrodes 111c-3 of the plurality of cells 111c in the transducer element 111b.

The lower electrodes 111c-3 of the plurality of cells 111c configuring the transducer element 111b may be connected in parallel to each other through the lines l, and receive pulses from the integrated circuit 112 or transmit electrical signals to the integrated circuit 1112.

The connection relation between the lower electrodes 111c-3 of the plurality of cells 111c will be described in detail with reference to FIG. 8, later.

The upper electrode 111c-5 may be disposed on the piezoelectric device 111c-1, and a ground voltage or a direct current voltage may be applied to the upper electrode 111c-5.

Due to the parallel connections between the cells 111c, the ground voltage or the direct current voltage may be applied in common to the upper electrodes 111c-5 of the plurality of cells 111c configuring the transducer element 111b.

The upper electrodes 111c-5 of the plurality of cells 111c may be connected in parallel to each other through the lines l. The ground voltage or the direct current voltage may be applied to the upper electrodes 111c-5 from the integrated circuit 112 connected to the upper electrodes 111c-5.

The connection relation between the upper electrodes 111c-5 of the plurality of cells 111c will be described in detail with reference to FIG. 8, later.

The piezoelectric device 111c-4 may be interposed between the lower electrode 111c-3 and the upper electrode 111c-5, and vibrate vertically according to pulses that are applied to the lower electrode 111c-3 to generate ultrasonic waves.

The piezoelectric device 111c-4 may be made of thin-film lead zirconate titanate (PZT) or Aluminum Nitride (AlN) having a thickness of, for example, 2.5 μm or less.

Figure 7:
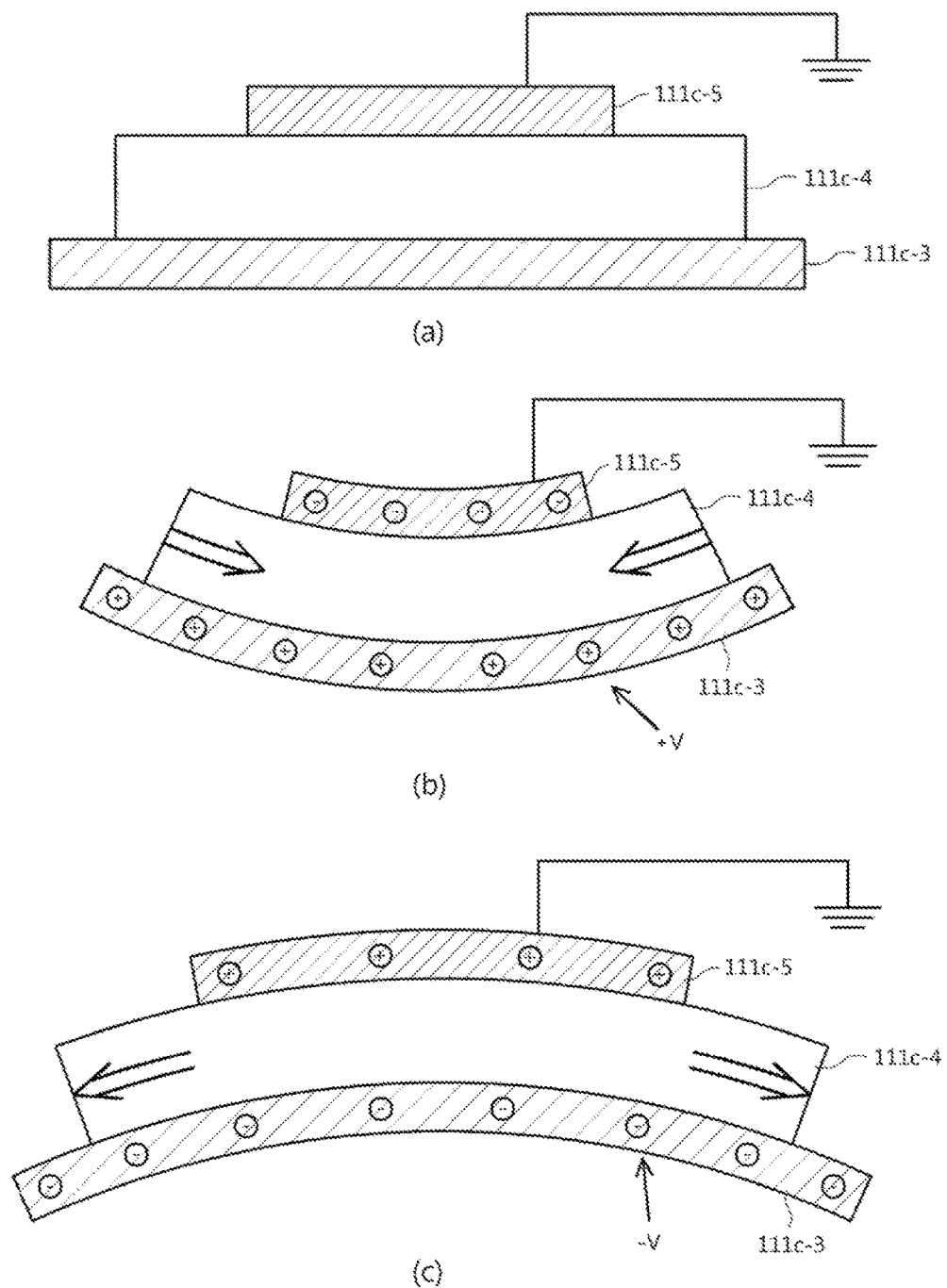
FIG. 7 is a view for describing the vibration principle of a piezoelectric device.

FIG. 7 is a view for describing the vibration principle of a piezoelectric device.

In FIG. 7, it is assumed that the upper electrode 111c-5 is connected to the ground.

The thickness of the piezoelectric device 111c-4 may be adjusted according to an applied voltage. Also, the area of the upper electrode 111c-5 may occupy 70% or less of the area of the piezoelectric device 111c-4.

Referring to (a) of FIG. 7, when no voltage is applied to the lower electrode 111c-3, the piezoelectric device 111c-4 may be maintained at its original horizontal position and original thickness. The original thickness of the piezoelectric device 111c-4 may be, for example, 2.5 μm or less.

Referring to (b) of FIG. 7, if a positive voltage +V is applied to the lower electrode 111c-3, the piezoelectric device 111c-4 may contract in a traverse direction that is parallel to the board element 111c-1, and the membrane part 111c-1b may vibrate downward by the contraction of the piezoelectric device 111c-4.

Referring to (c) of FIG. 7, if a negative voltage −V is applied to the lower electrode 111c-3, the piezoelectric device 111c-4 may expand in the traverse direction, and the membrane part 111c-1b may vibrate upward by the expansion of the piezoelectric device 111c-4.

Accordingly, when an alternating current voltage (that is, pulses) is applied to the lower electrode 111c-3, the piezoelectric device 111c-4 may expand and contract in the traverse direction according to positive and negative voltages appearing alternately. Due to the expansion and contraction of the piezoelectric device 111c-4, the membrane part 111c-1b may vibrate vertically so that ultrasonic waves are irradiated to an object according to the vibration frequency.

Meanwhile, when the membrane part 111c-1b receives echo ultrasonic waves and vibrates vertically at a vibration frequency, the piezoelectric device 111c-4 may expand and contract in the traverse direction. Due to the expansion and contraction of the piezoelectric device 111c-4, an electric field may be formed in the lower electrode 111c-3, and accordingly, the lower electrode 111c-3 outputs an electrical signal according to the vibration frequency.

In order to expand and contract the piezoelectric device 111c-4, the lower electrode 111c-3 may be connected to the integrated circuit 112 to receive pulses from the integrated circuit 112 upon irradiation of ultrasonic waves or to output an electrical signal to the integrated circuit 112 upon reception of ultrasonic waves.

Hereinafter, the connection relation between the plurality of cells 111c will be described in detail with reference to FIG. 8.

Figure 8:
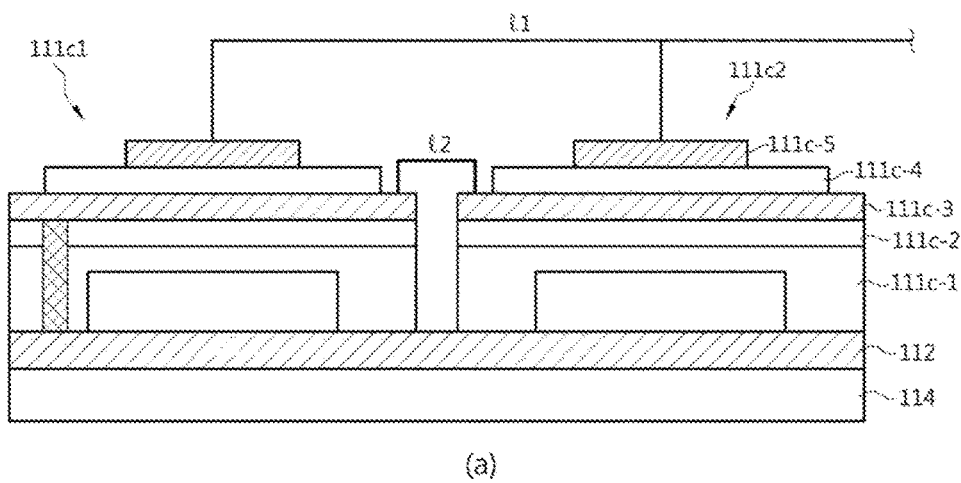
FIG. 8 is a conceptual diagram of a plurality of cells connected in parallel.
Figure 8:
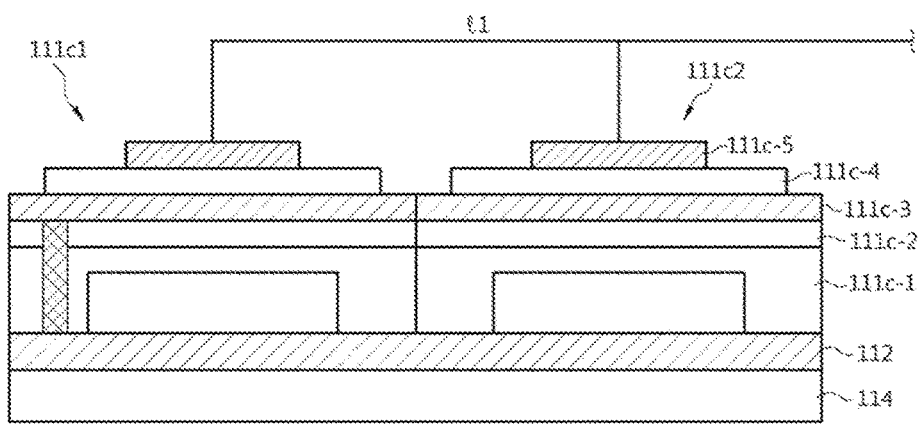

FIG. 8 is a conceptual diagram of a plurality of cells connected in parallel.

Referring to (a) of FIG. 8, a first cell 111c1 may be spaced apart from and connected in parallel to a second cell 111c2 on an integrated circuit 112. The upper electrode 111c-5 of the first cell 111c1 may be connected in parallel to the upper electrode 111c-5 of the second cell 111c2 through a line l1. Also, the lower electrode 111c-3 of the first cell 111c1 may be connected in parallel to the lower electrode 111c-3 of the second cell 111c2 through a line l2.

In the following description, it is assumed that a transducer array 111 is configured with a plurality of transducer elements 111b of a first element, a second element, a third element, and a fourth element.

The upper electrodes 111c-5 of a first cell 111c1 and a second cell 111c2 configuring the first element may be connected in parallel to the upper electrodes 111c-5 of first cells 111c1 and second cells 111c2 configuring the second to fourth elements.

That is, all the upper electrodes of the plurality of cells 111c included in the first to fourth elements may be connected in parallel to each other.

The lower electrodes 111c-3 of the first cell 111c1 and the second cell 111c2 configuring the first element may be connected in parallel to each other in the first element, without being connected in parallel to the lower electrodes 111c-3 of the first cells 111c1 and the second cells 111c2 configuring the second to fourth elements.

The lower electrodes 111c-3 of the first cell 111c1 and the second cell 111c2 configuring the second element may also be connected in parallel to each other in the first element, without being connected in parallel to the lower electrodes 111c-3 of the first cells 111c1 and the second cells 111c2 configuring the first, third, and fourth elements. Also, the lower electrodes 111c-3 of the first cells 111c1 and the second cells 111c2 configuring the third and fourth elements may be connected in the same way as described above.

That is, the lower electrodes of the plurality of cells 111c included in the first to fourth elements may be connected in parallel to each other only in the corresponding elements 111b.

In (a) of FIG. 8, the upper electrodes 111c-5 and the lower electrodes 111c-3 of the first cell 111c1 and the second cell 111c2 are respectively connected through the lines l1 and l2, however, the upper electrode 111c-5 and the lower electrode 111c-3 of the first cell 111c1 may be respectively connected directly to the upper electrode 111c-5 and the lower electrode 111c-3 of the second cell 111c2.

Also, in FIG. 8, the first cell 111c1 is spaced apart from the second cell 111c2 on the integrated circuit 112, however, the first cell 111c1 may contact the second cell 111c2. If the first cell 111c1 contacts the second cell 111c2, the upper electrode 111c-5 of the first cell 111c1 may be connected to the upper electrode 111c-5 of the second cell 111c2 through a line l1, and the lower electrode 111c-3 of the first cell 111c1 may be connected directly to the lower electrode 111c-3 of the second cell 111c2, as shown in (b) of FIG. 8.

Also, the lower electrode 111c-3 of the first cell 111c1 may be connected to the electrode of the integrated circuit 112 through flip-chip bonding. However, the upper electrode 111c-5 may also be connected directly to the integrated circuit 112, and both the first cell 111c1 and the second cell 111c2 may be connected directly to the integrated circuit 112.

According to another exemplary embodiment, the transducer element 111b may further include a separate path for connecting the plurality of cells 111c in parallel to each other. This other exemplary embodiment will be described with reference to FIG. 9, below.

Figure 9:
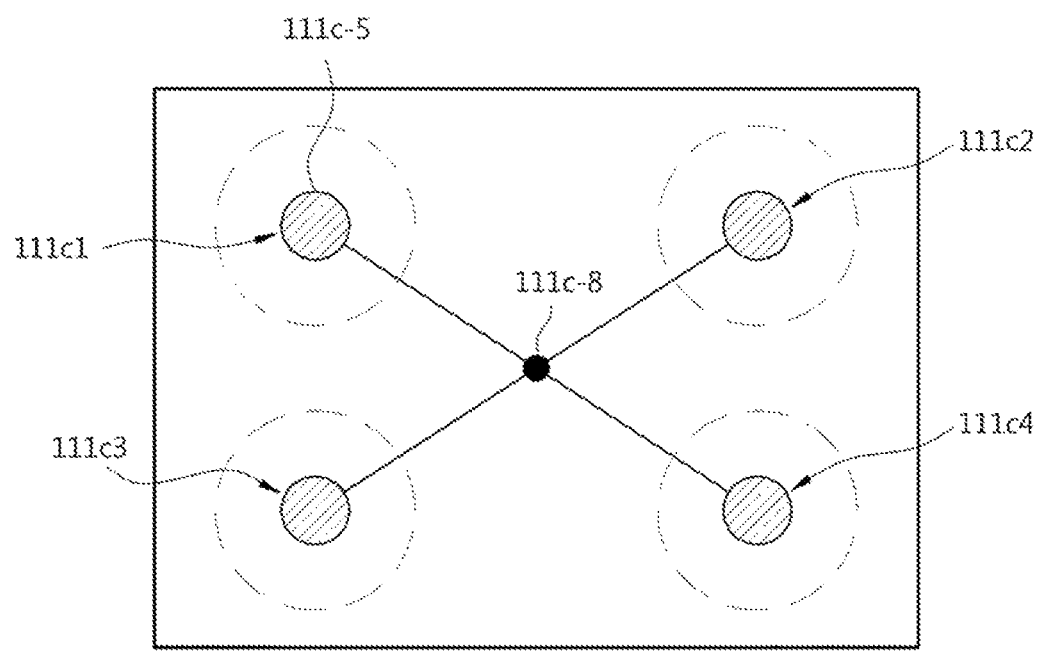
FIG. 9 is a front view of a transducer element according to another exemplary embodiment.

FIG. 9 is a front view of a transducer element according to another exemplary embodiment of the present disclosure.

Referring to FIG. 9, a transducer element 111b may further include a via 111c-8 that acts as a connection path for connecting the upper electrodes 111c-5 or the lower electrodes 111c-3 of a plurality of cells 111c1, 111c2, 111c3, and 111c4 configuring the transducer element 111b.

As shown in FIG. 9, the upper electrodes 111c-5 of the plurality of cells 111c1 to 111c4 may be connected to the via 111c-8 through lines l1, and the via 111c-8 may be connected to the ground or a direct current voltage source.

Also, the lower electrodes 111c-3 of the plurality of cells 111c1 to 111d4 may also be connected to the via 111c-8 through lines l2, and the via 111c-8 may be connected to an integrated circuit 112.

In this case, the via 111c-8 connected to the upper electrodes 111c-5 may be different from the via 111c-8 connected to the lower electrodes 111c-3, although is not limited thereto.

As such, the plurality of cells 111c may be connected in parallel to each other so that pulses can be applied in common to the cells 111c or the cells 111c can output electrical signals.

Hereinafter, a process in which signals that are applied to or output from a plurality of cells 111c included in a transducer element 111b are transferred will be described in detail with reference to FIG. 10.

Figure 10:
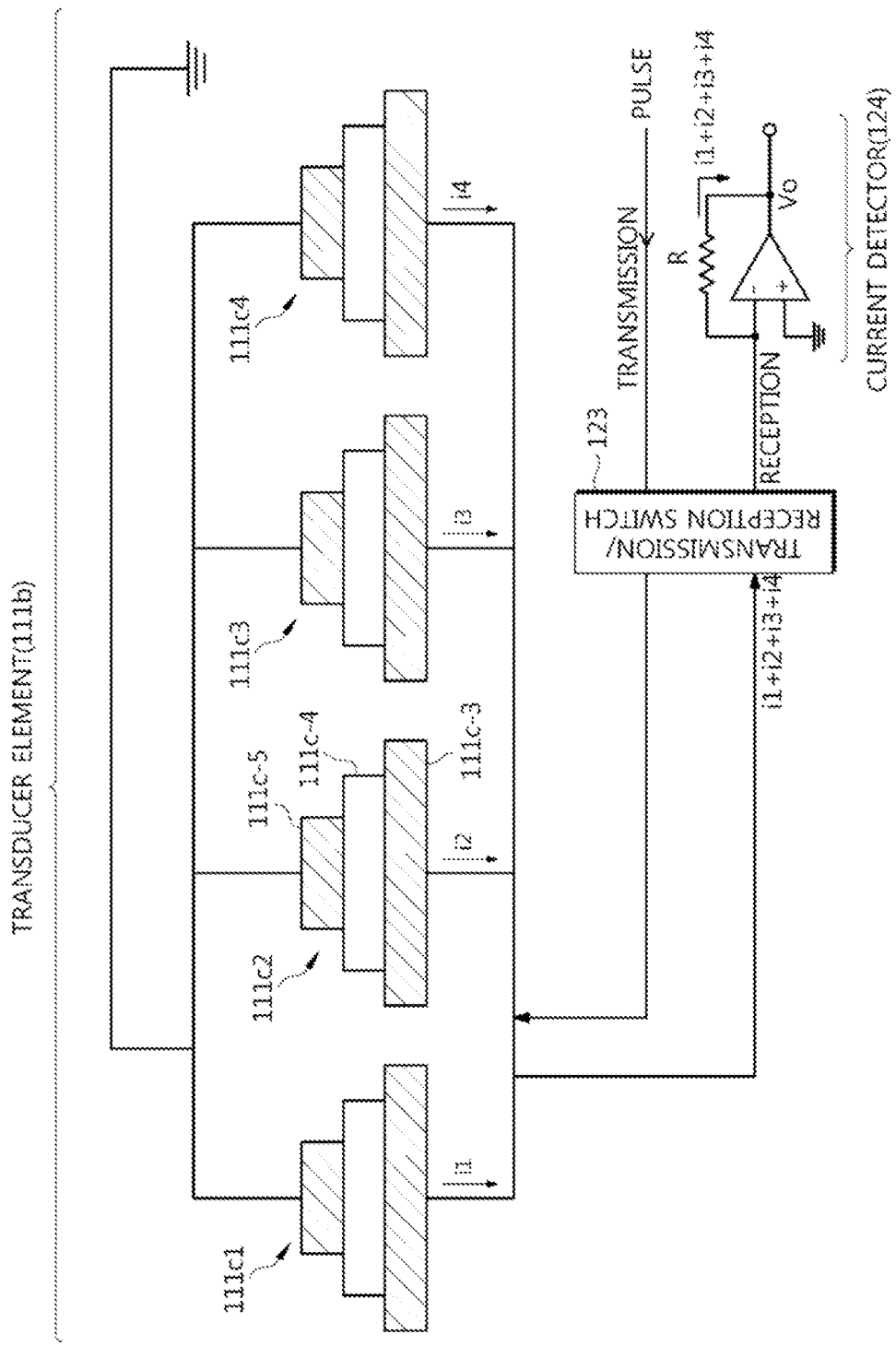
FIG. 10 is a view for describing a process in which transmission and reception signals are transferred in a transducer element.

FIG. 10 is a view for describing a process in which transmission and reception signals are transferred in a transducer element.

Referring to FIGS. 2, 3, and 10, the upper electrodes 111c-5 of a plurality of cells 111c connected in parallel to each other (for example, a first cell 111c1, a second cell 111c2, a third cell 111c3, and a fourth cell 111c4) of each transducer element 111b may be connected to the ground through lines l1, and the lower electrodes 111c-3 of the cells 111c may be connected to the current detector 124 through the integrated circuit 112.

The integrated circuit 112 may be coupled with a plurality of cells 111c configuring one or more transducer elements 111b through flip-chip bonding to electrically connect to the upper electrodes 111c-5 and the lower electrodes 111c-3 of the plurality of cells 111c.

In a transmission mode, the transmission/reception switch 123 may transfer pulses received from the pulser 121 and the pulse delay unit 122 to the transducer element 111b, and in a reception mode, the transmission/reception switch 123 may transfer an electrical signal received from the transducer element 111b to the current detector 124.

The current detector 124, which may be implemented as an amplifier, may receive a current from a plurality of cells 111c configuring each transducer element 111b and connected in parallel to each other. Accordingly, there may be provided a plurality of amplifiers 124 corresponding to the number of the transducer elements 111b included in the transducer module 110.

If a current generated by the first cell 111c1 is referred to as i1, a current generated by the second cell 111c2 is referred to as i2, a current generated by the third cell 111c3 is referred to as i3, and a current generated by the fourth cell 111c4 is referred to as i4, the current detector 124 may receive a sum (i1+i2+i3+i4) of i1, i2, i3, and i4 as an input signal since the first to fourth cells 111c1 to 111c4 are connected in parallel to each other.

The current detector 124 may be implemented as an inverting amplifier to output a product (R*(i1+i2+i3+i4)) of the sum (i1+i2+i3+i4) and R stored in the inverting amplifier, as a voltage Vo.

The current detector 124 may measure a voltage difference between the upper electrodes 111c-5 and the lower electrodes 111c-3 of the plurality of cells 111c configuring the transducer element 111b to thereby detect a current output from the cells 111c. In this case, the current detector 124 may be implemented as an amplifier to amplify the voltage difference between the upper electrodes 111c-5 and the lower electrodes 111c-3.

Hereinafter, a method of controlling the ultrasound imaging apparatus 10 will be described with reference to FIG. 11.

FIG. 11 is a flowchart illustrating a method of controlling an ultrasound imaging apparatus, according to an exemplary embodiment.

Referring to FIGS. 2, 6, 10, and 11, the transmission/reception switch 123 may operate in a transmission mode according to a control signal from the system controller 240, and the pulser 121 may apply pulses to a plurality of cells 111c included in each transducer element 111b, in operation S1110. At this time, an alternating current voltage generated by the pulser 121 may be delayed by the pulse delay unit 122. The delayed alternating current voltage may be applied to the lower electrodes 111c-3 of the cells 111c connected in parallel to each other, while a ground voltage or a direct current voltage may be applied to the upper electrodes 111c-5 of the cells 111c connected in parallel to each other.

Next, ultrasonic waves may be generated by vibration of the piezoelectric device 111c-4 and the membrane part 111c-1b included in each cell 111c, and the ultrasonic waves may be irradiated to a target region of an object, in operation S1120.

Next, the transmission/reception switch 123 may operate in a reception mode according to a control signal from the system controller 240. A plurality of cells 111c included in each transducer element 111b of the transducer module 110 may receive echo ultrasonic waves, and convert the received echo ultrasonic waves into electrical signals, in operation S1130. More specifically, the piezoelectric device 111c-4 and the membrane part 111c-1b may vibrate mechanically by the echo ultrasonic waves reflected from the object ob so that the piezoelectric device 111d is polarized to discharge electric charges to the lower electrodes 111c-3. Accordingly, the lower electrodes 111c-3 may output a voltage and a current as an electrical signal.

Next, the current detector 124, which is implemented as an amplifier, may receive currents output from a plurality of cells 111c included in each transducer element 111b and connected in parallel to each other, and output a voltage based on a sum of the currents, in operation S1140. The voltage output from the current detector 124 may be proportional to the sum of the currents output from the plurality of cells 111c.

Next, the echo delay unit 126 may delay electrical signals output from the individual transducer elements 111b included in the transducer module 110, according to a focused point and a steering angle, the adder 127 may perform beamforming of adding the electrical signals from the individual transducer elements 111b included in the transducer module 110, the electrical signals delayed by the echo delay unit 126, to focus the result of the addition into an electrical signal, the signal processor 220 may perform signal processing on the focused electrical signal, and the image processor 230 may perform image processing on the signal-processed signal, in operation S1150.

Before the beamforming is performed, the analog-to-digital converter 125 may convert an analog voltage output from the current detector 124 into a digital signal, and then transmit the digital signal to the echo delay unit 126.

The beamforming, signal processing, and image processing have been described above, and accordingly, detailed descriptions thereof will be omitted.

Next, the display unit 300 may display an ultrasound image created by the image processor 230, in operation S1160.

As such, by configuring each transducer element with a plurality of cells, it is possible to reduce the thicknesses of piezoelectric devices, and to realize good broadband characteristics of the transducer elements with the thin piezoelectric devices.

For example, when the piezoelectric devices are made of thin-film PZT having a thickness of 2.5 μm or less, it is possible to realize good broadband characteristics of 90% or more.

Also, if a voltage is applied to a cell upon irradiation of ultrasonic waves, the same voltage is applied to a plurality of cells connected in parallel to the cell so that the plurality of cells can be driven with a low voltage.

Also, when currents output from a plurality of cells connected in parallel to each other are different from each other upon reception of ultrasonic waves, different electrical signals are generated based on the different currents from the individual cells, resulting in improvement of the receiving sensitivity of echo ultrasonic waves.

Therefore, in the ultrasound probe and the ultrasound imaging apparatus according to the exemplary embodiments as described above, since each transducer element is configured with a plurality of cells, it is possible to reduce the thickness of the piezoelectric device, and to realize good broadband characteristics.

Also, since a voltage is applied in common to a part of a plurality of cells connected in parallel to each other in each transducer element, it is possible to drive a plurality of cells with a low voltage.

Also, since each transducer element generates an electrical signal based on currents output from a plurality of cells connected in parallel to each other upon reception of ultrasonic waves, it is possible to improve the receiving sensitivity of echo ultrasonic waves that are received by the individual cells.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. A probe comprising:
   a transducer array comprising a first transducer element comprising first cells connected in parallel to each other; and
   a current detector configured to apply a voltage to the first cells in a transmission mode, and to output an electrical signal based on currents output from the first cells in a reception mode,
   wherein each of the first cells comprises:
      a thin-film piezoelectric device,
      an upper electrode disposed at an upper surface of the thin-film piezoelectric device, and
      a lower electrode disposed at a lower surface of the thin-film piezoelectric device,
      wherein the upper electrode and the lower electrode included in one first cell, among the first cells, are spaced apart from the upper electrode and the lower electrode, respectively, that are included in other first cell, among the first cells, so that the one first cell and the other first cell are spaced apart from each other.

2. The probe according to claim 1, wherein the first transducer element comprises a piezoelectric micromachined ultrasonic transducer (pMUT) element which includes the thin-film piezoelectric device, and
   the transducer array comprises a pMUT array.

3. The probe according to claim 1, wherein the thin-film piezoelectric device comprises thin-film lead zirconate titanate (PZT) having a thickness of 2.5 μm or less.

4. The probe according to claim 1, wherein the upper electrodes of the first cells are connected in parallel to upper electrodes of second cells comprised in a second transducer element, and
   the lower electrodes of the first cells are connected in parallel to each other.

5. The probe according to claim 4, wherein the upper electrodes of the first cells and the second cells are configured to receive a ground voltage or a direct current voltage applied in common to the upper electrodes of the first cells and the second cells.

6. The probe according to claim 4, wherein the lower electrodes of the first cells and the second cells are connected to the current detector.

7. The probe according to claim 1, wherein the current detector is configured to detect a voltage difference between the upper electrode and the lower electrode of each of the first cells.

8. The probe according to claim 1, wherein each of the first cells further comprises a board member provided on a side of the lower electrode that is distal to the upper electrode, the board member being configured to support the lower electrode.

9. The probe according to claim 8, wherein the board member is formed of silicon (Si) and comprises:
   a membrane part formed in a center of the board member, and
   a fixing support part formed along edges of the board member, so that a cavity is formed between the membrane part and the fixing support part, and
   wherein the thin-film piezoelectric device expands or contracts in a traverse direction according to a voltage applied to the lower electrode of each of the first cells to vibrate the membrane part.

10. The probe according to claim 9, wherein an area of the upper electrode of each of the first cells occupies 70% or less of an area of the membrane part.

11. The probe according to claim 1, wherein the first transducer element comprises a via configured to connect the upper electrodes of the first cells to each other or to connect the lower electrodes of the first cells to each other.

12. The probe according to claim 1, wherein the first transducer element comprises four cells or nine cells.

13. The probe according to claim 1, wherein the current detector comprises an amplifier configured to output the electrical signal generated based on a voltage that is proportional to a sum of the currents output from the first cells.

14. The probe according to claim 1, wherein the current detector comprises an amplifier including:
   an input connected to the lower electrode of each of the first cells and configured to receive a sum of the currents being individually output by each of the first cells, and
   an output configured to output the electrical signal generated based on a voltage that is proportional to the sum of the currents.

* * * * *